US010215641B2

(12) United States Patent
Frick

(10) Patent No.: US 10,215,641 B2
(45) Date of Patent: Feb. 26, 2019

(54) COLOR MEASURING APPARATUS

(71) Applicant: X-Rite Switzerland GmbH, Regensdorf (CH)

(72) Inventor: Beat Frick, Buchs (CH)

(73) Assignee: X-Rite Switzerland GmbH, Regensdorf (CH)

( * ) Notice: Subject to any disclaimer, the term of this patent is extended or adjusted under 35 U.S.C. 154(b) by 0 days.

(21) Appl. No.: 14/798,920

(22) Filed: Jul. 14, 2015

(65) Prior Publication Data

US 2016/0011052 A1     Jan. 14, 2016

(51) Int. Cl.
*G01J 3/50*     (2006.01)
*G01J 3/02*     (2006.01)
(Continued)

(52) U.S. Cl.
CPC ............. *G01J 3/501* (2013.01); *G01J 3/0297* (2013.01); *G01J 3/10* (2013.01); *G01J 3/504* (2013.01);
(Continued)

(58) Field of Classification Search
CPC .... G01J 3/501; G01J 3/524; G01J 3/10; G01J 3/504; G01N 21/57; G01N 2021/575
See application file for complete search history.

(56) References Cited

U.S. PATENT DOCUMENTS 4,755,058 A * 7/1988 Shaffer ................ G01N 21/474
356/408
4,917,495 A * 4/1990 Steenhoek ............ G01J 3/0251
356/328

(Continued)

FOREIGN PATENT DOCUMENTS

EP     1314972 A1    5/2003
EP     1914529 A1    4/2008
(Continued)

OTHER PUBLICATIONS

Kettler, W. H., Geräteprofilierung: Management Globaler Farbkonsistenz, DFO Tagung Qualitätssicherung und Prüfverfahren, 2008: English: Instrument Profiling: Managing Global Colour Consistency, DFO Meeting Quality Assurance and Test Methods, 2008, 21 pages.

Hertzsch, et al., A Simple Technique for Optical Thin Film Characterisation in the Case of Small Refractive Index Differences Between the Coating and the Substrate, Glass Technology: European Journal of Glass Science and Technology Part A, vol. 49, No. 1, , pp. 41-46, Feb. 2008.

(Continued)

*Primary Examiner* — Maurice Smith
(74) *Attorney, Agent, or Firm* — Hahn Loeser & Parks LLP

(57) ABSTRACT

A color measuring apparatus includes a measurement assembly which includes at least one illumination assembly for applying substantially parallel illumination light to a measurement spot of a measurement object and a pick-up assembly for capturing the measurement light radiated back from the measurement spot in an observation direction and for converting the same into corresponding electrical signals. The illumination assembly includes at least two illumination subassemblies which illuminate the measurement spot from different illumination sub-directions near a first preset nominal illumination direction, each with preferably parallel illumination light. By the illumination from different illumination sub-directions slightly deviating from the nominal illumination direction, angular errors of the illumination assembly can be compensated for in a simple manner.

18 Claims, 6 Drawing Sheets

(51) Int. Cl.
*G01J 3/10* (2006.01)
*G01J 3/52* (2006.01)
*G01N 21/57* (2006.01)

(52) U.S. Cl.
CPC .............. *G01J 3/524* (2013.01); *G01N 21/57* (2013.01); *G01N 2021/575* (2013.01)

(56) References Cited

U.S. PATENT DOCUMENTS

| | | | | |
|---|---|---|---|---|
| 5,028,139 | A * | 7/1991 | Kramer | G01N 21/474 356/446 |
| 5,150,174 | A * | 9/1992 | Ryczek | G01J 3/50 250/226 |
| 5,837,546 | A * | 11/1998 | Allen | G01N 33/5438 422/403 |
| 6,707,553 | B1 * | 3/2004 | Imura | G01J 3/10 356/402 |
| 7,262,854 | B2 | 8/2007 | Imura | |
| 7,929,142 | B2 * | 4/2011 | Ben-Ezra | G01N 21/474 356/445 |
| 2005/0062964 | A1 * | 3/2005 | Guttman | G01J 3/2803 356/319 |
| 2006/0033922 | A1 * | 2/2006 | Sperling | G01J 3/504 356/446 |
| 2006/0192957 | A1 * | 8/2006 | Frick | G01J 3/02 356/328 |
| 2006/0274316 | A1 * | 12/2006 | Perquis | G01J 3/46 356/446 |
| 2007/0201029 | A1 * | 8/2007 | Jinno | G01N 21/57 356/446 |
| 2008/0180950 | A1 * | 7/2008 | Kang | A61B 5/0059 362/249.16 |
| 2010/0220478 | A1 * | 9/2010 | Fields | B64F 1/20 362/237 |
| 2011/0141476 | A1 | 6/2011 | Schmaelzle et al. | |
| 2013/0226330 | A1 * | 8/2013 | Sopori | G01N 21/00 700/117 |
| 2013/0265568 | A1 * | 10/2013 | Micheels | G01N 21/359 356/51 |
| 2014/0152990 | A1 * | 6/2014 | Ehbets | G01J 3/50 356/405 |

FOREIGN PATENT DOCUMENTS

EP 2703789 A1 3/2014
EP 2728342 A1 5/2014

OTHER PUBLICATIONS

Germain, et al., Optical Explosives Detection: From Color Changes to Fluorescence Turn-On, The Royal Societ of Chemistry, Chemical Society Review, 38, pp. 2543-2555, 2009.
Kettler, W. H., Colour Management in Paint Applications, Nov. 14, 2014, Wuppertal Germany, 50 pages.
European Search Report for European Patent Application No. 14176865.5 with English translation dated Dec. 2, 2014.

* cited by examiner

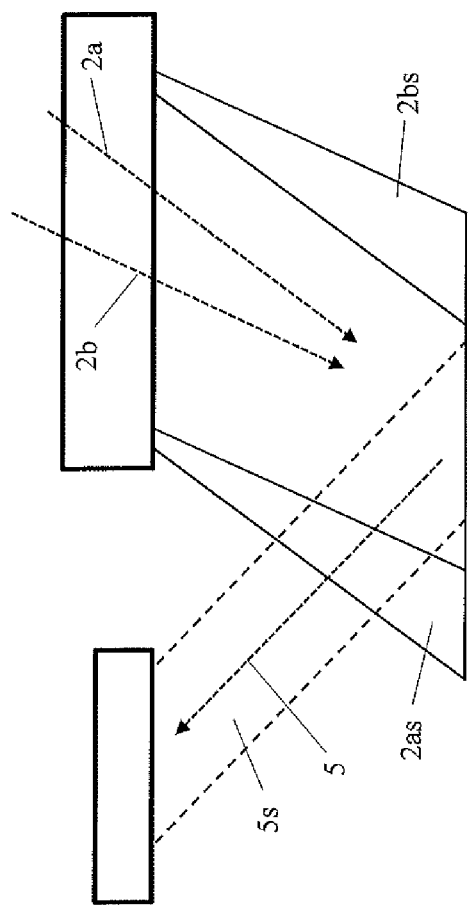
Fig. 4
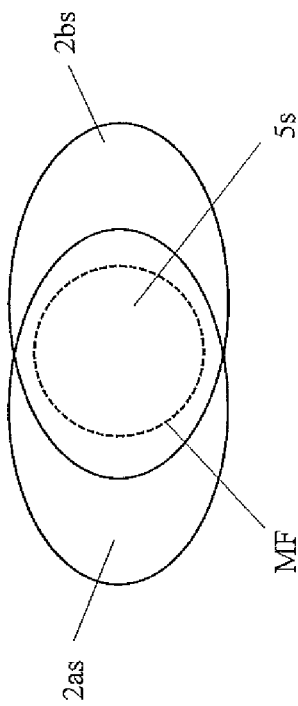
Fig. 5
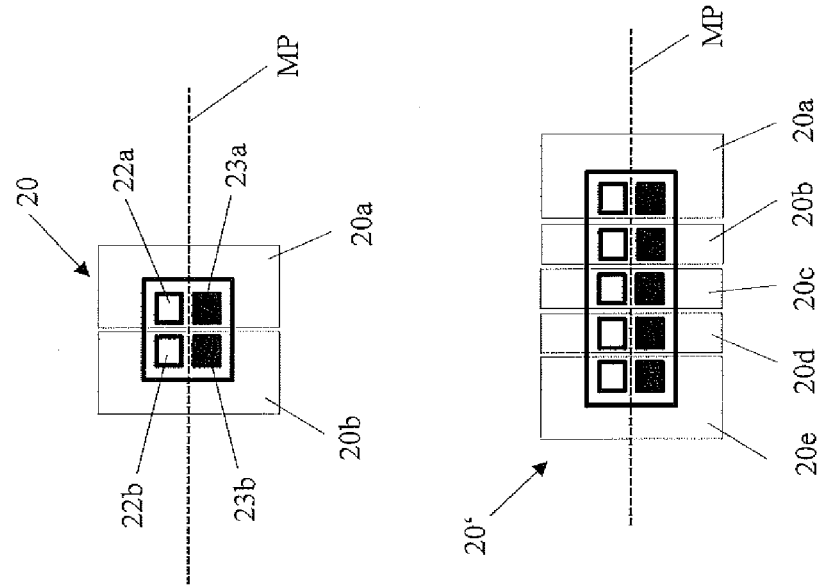
Fig. 3
Fig. 8

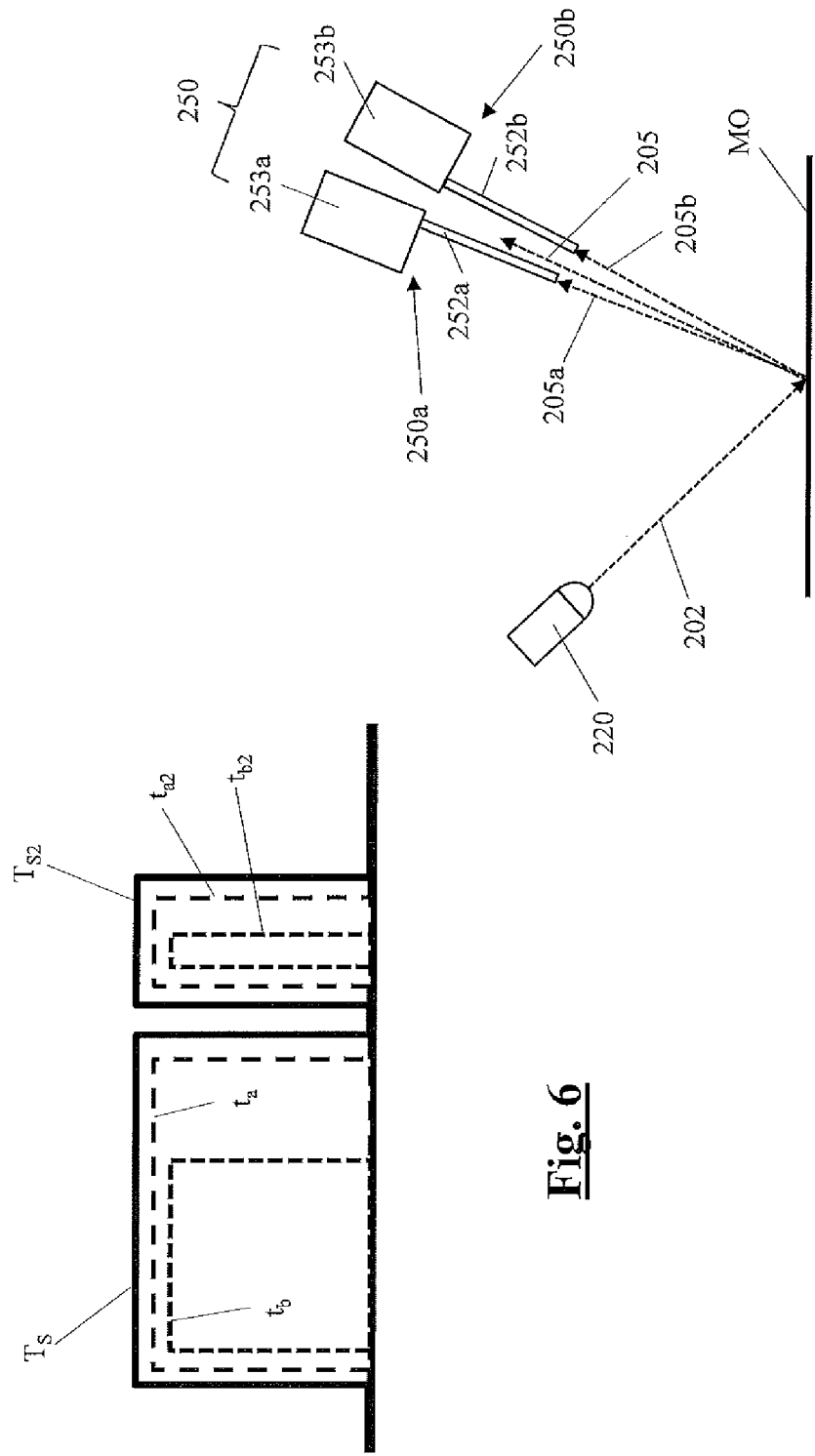

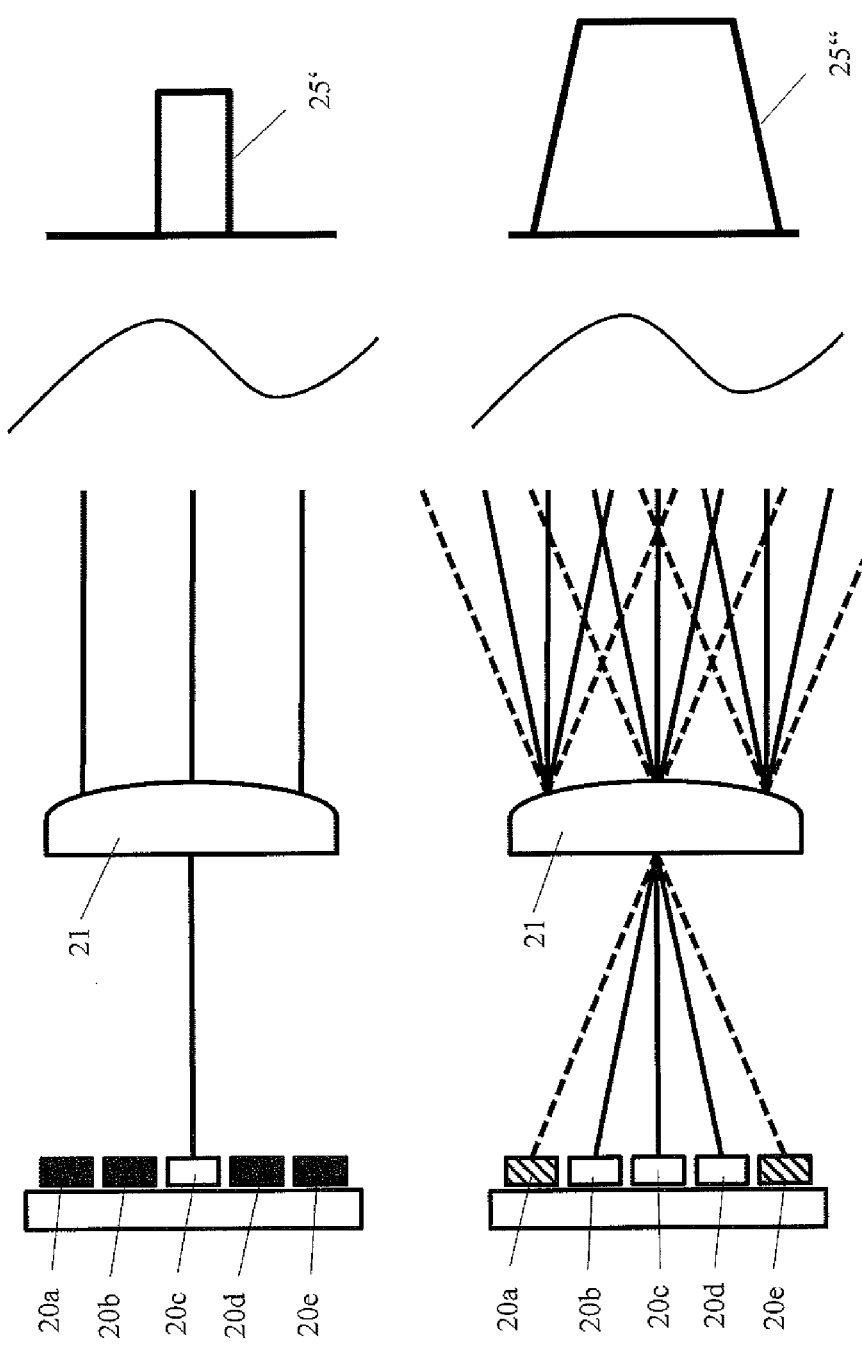

COLOR MEASURING APPARATUS

BACKGROUND

1. Technical Field

The present disclosure relates generally to color measuring apparatus with a measurement assembly which includes at least one illumination assembly for applying preferably substantially parallel illumination light to a measurement spot of a measurement object and a pick-up assembly for capturing the measurement light radiated back from the measurement spot and for converting the same into corresponding electrical signals. The disclosed color measuring apparatus can be formed as autonomous apparatus or as measurement periphery for employment in connection with a controlling computer evaluating measurement data independently of the underlying measurement technology. Autonomous color measuring apparatus generally include all of the control and display organs required for the measurement operation as well as their own current supply and moreover are frequently also equipped with an interface for communication with a computer, wherein both measurement data and control data can be exchanged with the computer. Color measuring apparatus configured as measurement periphery usually do not have their own control and display organs and are—like each other computer peripheral—controlled by a superordinated computer. For communication with a computer, modern color measuring apparatus are often, e.g., fitted with a so-called USB (Universal Serial Bus) interface, via which the current supply can also be effected at the same time in many cases (from the connected computer).

2. Background Art

Nowadays, metallic colors and varnishes with effect pigments are more and more employed not only in the automotive industry. Such colors exhibit a severe angular dependency. Varnishes with aluminum flakes for example exhibit a severe brightness flop. Varnishes with interference effect pigments additionally also exhibit color differences with varied observation or illumination direction. For measuring such varnishes, multi-angle measuring apparatus have been established. The gloss measurement is a related issue, in which the measurement result is also sensitive to angle.

Measuring apparatus which are able to acquire such characteristics have to be adapted to illuminate the measurement object in one or more different, exactly defined illumination directions (nominal illumination directions) and to pick up the light radiated back from the measurement object from at least one exactly defined observation direction (nominal observation direction). Observation direction and illumination direction can be exchanged. Color measuring apparatus of this type are, e.g., described in great detail in the documents EP 2 703 789 A1 and EP 2 728 342 A1.

In the publication "Geräteprofilierung: Management globaler Farbkonsistenz" of Wilhelm H. Kettler, DFO Tagung Qualitatssicherung und Prüfverfahren, 2008, various causes are set out, which can result in measurement errors in the employment of such color measuring apparatus. In particular, the so-called systematic errors, which are attributable to certain apparatus imperfections such as erroneous calibration belong thereto. In a lecture delivered by Wilhelm H. Kettler for Farbe und Lack II Seminare Modul 2: Tiefere Einblicke in die Farbmetrik Jun. 25-27, 2014, Stuttgart (FPL) with the title "Farbmanagement", the so-called angular errors are in particular also indicated, which can arise by the geometric conditions of the illumination and observation beam paths as well as by the apertures of the illumination and observation beam paths. Angular errors especially effect particularly severely in the measurement on samples with effect colors.

The present invention primarily deals with avoiding and compensating for measurement errors caused by such angular errors, respectively.

Therefore, by the present invention, a color measuring apparatus of the generic type is to be improved to the effect that angular errors can be simply corrected such that the illumination and observation directions preset by the respective measurement geometry are exactly complied with and thereby measurement value corruptions are avoided.

This object underlying the invention is equally solved by the color measuring apparatus according to the invention characterized by the features of the independent claim 1 or by the features of the independent claim 14. Advantageous configurations and developments of the color measuring apparatus according to the invention are the subject matter of the dependent claims.

SUMMARY

The nature of the first form of realization of the invention is in the following: a color measuring apparatus has a measurement assembly including at least one illumination assembly for applying substantially parallel illumination light to a measurement spot of a measurement object and a pick-up assembly for capturing the measurement light radiated back from the measurement spot in an observation direction and for converting the same into corresponding electrical signals. The illumination assembly includes at least two illumination subassemblies illuminating the measurement spot from different illumination sub-directions located near a first preset nominal illumination direction each with parallel illumination light. Advantageously, but not necessarily, therein, the illumination sub-directions enclose the first nominal illumination direction between them.

By the division of the illumination assembly in two or more illumination subassemblies, measurement errors caused by misalignment of the illumination assembly can be compensated for or avoided.

Conveniently, the illumination sub-directions are angularly offset to each other by an angle of maximally 4° to 8°.

Advantageously, the illumination assembly includes maximally five to seven illumination subassemblies, which illuminate the measurement spot from different illumination sub-directions near to each other and therein preferably, but not necessarily, enclose a nominal illumination direction between them.

According to an advantageous embodiment, the color measuring apparatus has at least one further illumination assembly, which illuminates the measurement spot substantially from a further preset nominal illumination direction different with respect to the first preset nominal illumination direction with parallel illumination light.

Therein, the at least one further illumination assembly advantageously includes at least two illumination subassemblies illuminating the measurement spot from different illumination sub-directions near the further preset nominal illumination direction each with parallel illumination light.

Conveniently, the illumination subassemblies each have a light source, which is composed of at least one, preferably two or more light emitting diodes with different emission spectra.

According to a further advantageous aspect of the invention, the color measuring apparatus has an electronic control for the illumination subassemblies and the pick-up assembly and the control is formed to separately control the illumination subassemblies within each one illumination assembly.

Advantageously, therein, the control is formed to individually control the activation durations of the illumination subassemblies each within one illumination assembly.

According to a further advantageous embodiment, the control is formed to activate the illumination assemblies or the illumination subassemblies thereof and the pick-up assembly for at least two differently long measurement durations.

Very particularly advantageously, the color measuring apparatus has means for calculating derivatives of the reflection factors for a nominal illumination angle for angular errors in the direction of the measurement plane.

The nature of the second form of realization of the color measuring apparatus according to the invention is in the following: a color measuring apparatus includes a measurement assembly including at least one illumination assembly for applying preferably substantially parallel illumination light to a measurement spot of a measurement object and at least one pick-up assembly for capturing the measurement light radiated back from the measurement spot and for converting the same into corresponding electrical signals. The at least one pick-up assembly in turn includes at least two pick-up subassemblies, which collect measurement light radiated back from the measurement spot from different observation sub-directions near a preset nominal observation direction. Advantageously, but not necessarily, therein, the observation sub-directions enclose the nominal observation direction between them.

By the division of the pick-up assembly in two or more pick-up subassemblies, measurement errors caused by misalignment of the pick-up assembly can be compensated for or avoided.

In the second form of realization of the invention, the roles of illumination of the measurement object and collection of the measurement light radiated back from the measurement object are exchanged, but the basic idea of the invention is obviously the same. Accordingly, the same analogously also applies to the number and orientation of the pick-up subassemblies as the facts mentioned to the illumination subassemblies. The mentioned control of the color measuring apparatus is correspondingly adapted to the control of the pick-up subassemblies in analogous manner.

Additional features, functions and benefits of the present disclosure will be apparent from the detailed description which follows, particularly when read in conjunction with the accompanying figures.

BRIEF DESCRIPTION OF THE FIGURES

In the following, the invention is explained in more detail based on the following figures.

FIG. 3 shows a schematic illustration of an illumination assembly of the color measuring apparatus of FIG. 2, FIG. 4 shows the beam paths of the illumination assembly of FIG. 3 in a side view, FIG. 5 shows the beam paths in a floor plan, FIG. 6 shows a diagram for explaining the principal measurement operation, FIG. 8 shows a schematic illustration of a variant of the illumination assembly of the color measuring apparatus of FIG. 2, FIGS. 9, 10 show two schematic sketches for explaining an aperture correction, and FIG. 11 shows a severely simplified schematic illustration of an embodiment of the second form of realization of the color measuring apparatus according to the invention.

DESCRIPTION OF EXEMPLARY EMBODIMENT(S)

Figure 1:
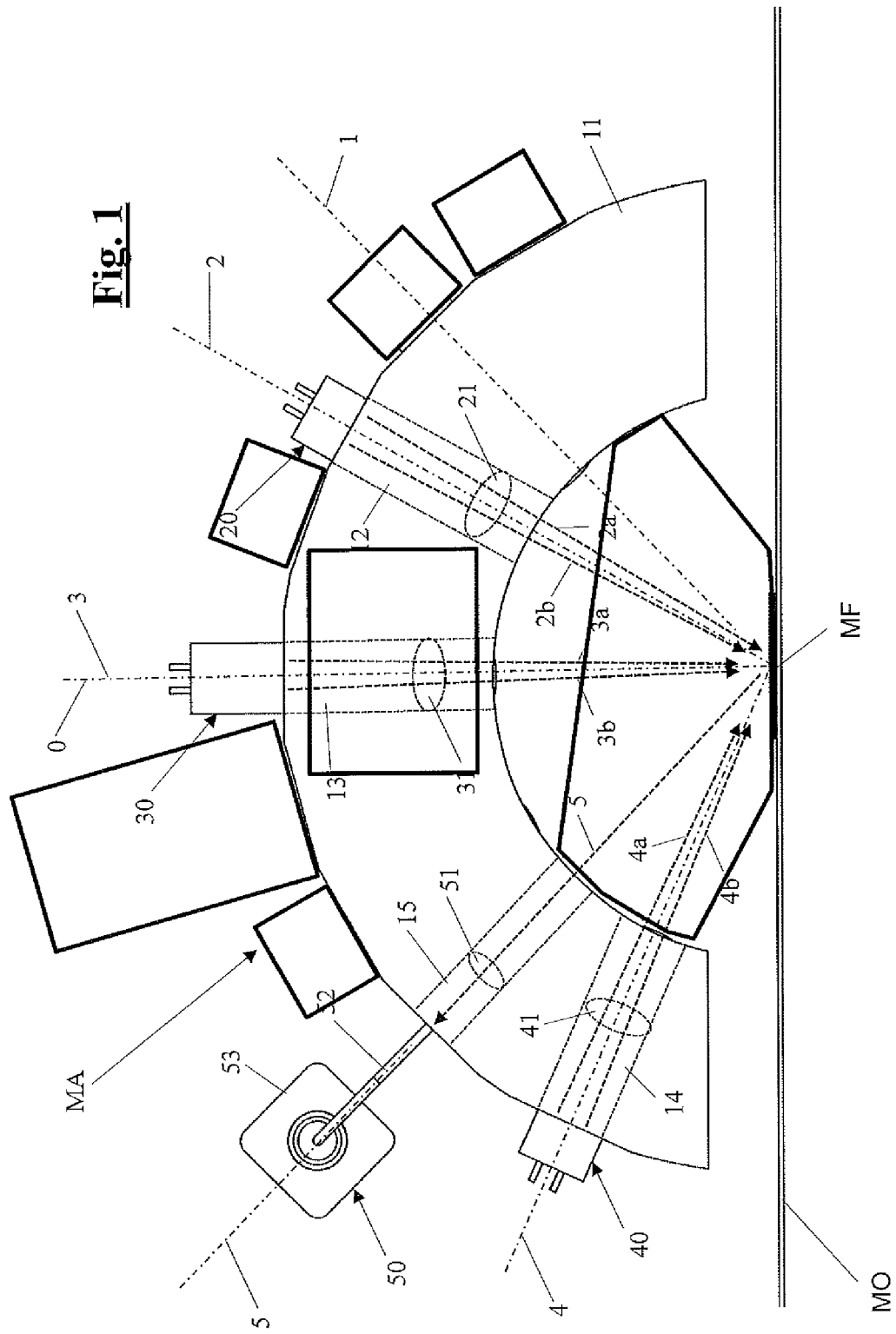
FIG. 1 shows a slightly simplified illustration of the basic construction of the first form of realization of the color measuring apparatus according to the invention.
Figure 2:
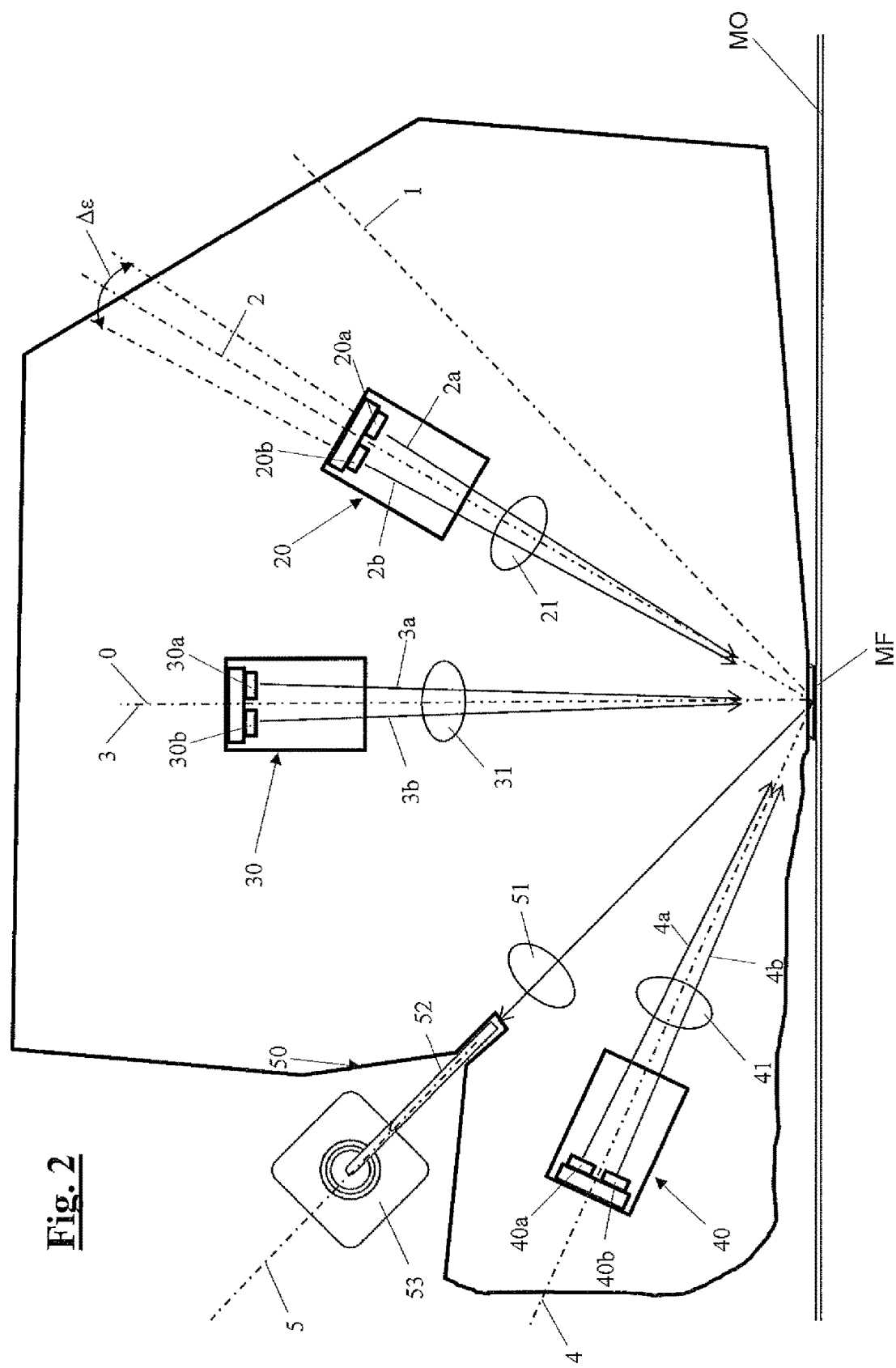
FIG. 2 shows a schematized illustration of the optical concept of the color measuring apparatus according to the invention of FIG. 1.

For the following description of figures, the following determination applies: if individual reference characters are not registered in a figure, thus, reference is made to the remaining figures and the associated description parts in this respect. By "measurement assembly", the entirety of those components of the color measuring apparatus is understood, which serve for illumination of a measurement spot on the surface of a measurement object and for capturing the light radiated back from this measurement spot and for converting the same into corresponding electrical signals. By "apparatus normal", an (imagined) line fixed to apparatus is to be understood, which (ideally) is perpendicular to the surface of the measurement object and defines the center of the measurement spot in practical employment of the color measuring apparatus. By "illumination direction", the direction is to be understood, in which the measurement spot is illuminated. Analogously, by "observation direction", the direction is to be understood, from which the measurement light radiated back from the measurement spot is picked up. By "nominal illumination directions" and "nominal observation direction", those illumination and observation directions, respectively, are to be understood, for which the color measuring apparatus is configured corresponding to its underlying measurement geometry. The actual illumination and observation directions can (slightly) deviate from the nominal illumination and observation directions e.g. due to manufacturing tolerances. By "specular direction", the nominal observation direction reflected on the surface of the (flat) measurement object is to be understood. Conventionally, the nominal illumination and observation directions are related to this specular direction. A multi-angle color measuring apparatus has multiple nominal illumination directions (and optionally also multiple nominal observation directions). By "measurement plane", a plane extending through the apparatus normal and all nominal illumination directions and the nominal observation direction as well as the specular direction is to be understood. All of the nominal angular specifications relate to directions located within the measurement plane.

In its general conception, the color measuring apparatus according to the invention is mostly similarly constructed as the apparatus disclosed in the initially mentioned documents EP 2 703 789 A1 and EP 2 728 342 A1. It includes a housing accommodating a measurement assembly and an electronic control. On the front side of the housing, a display assembly is provided. Further, control organs are disposed at the top of the housing. Laterally on the housing, there is an interface (preferably USB) for connecting the apparatus to an external computer. The housing has a measurement opening at the bottom, through which illumination light can exit the housing interior and inversely measurement light can enter the housing interior from the outside.

The basic formation of the measurement assembly located in the housing is apparent from FIG. 1. The measurement assembly overall denoted by MA includes a curved body 11 stationarily fixed in the housing, in which all of the optical and photo-electrical components of the measurement assembly MA, respectively, are disposed in four continuous chambers 12, 13, 14 and 15 in the shown embodiment. In the shown embodiment, these components are composed of three illumination assemblies 20, 30 and 40 and a pick-up assembly 50 with a spectrometer 53, to which the measurement light is supplied via a lens 51 and a light guide 52. The spectrometer 53 itself is located outside of the chamber 15. A lens 21, 31 and 41, respectively, is each associated with the illumination assemblies 20, 30 and 40. The three illumination assemblies 20, 30 and 40 illuminate a measurement spot MF on a measurement object MO via the associated lenses 21, 31 and 41 each with parallel radiation beams. The illumination assemblies 20, 30 and 40 are (except for slight tolerance deviations) each aligned with a preset nominal illumination direction 2, 3 and 4, respectively. The pick-up assembly is aligned with a preset nominal observation direction 5. The entire measurement assembly MA is arranged such that the nominal illumination directions and the nominal observation direction are in a common measurement plane MP, which also includes an apparatus normal denoted by 0. Further, the measurement plane also includes a specular direction 1, from which the angular positions of the nominal observation directions 2, 3 and 4 and the nominal observation direction 5 are measured as the reference direction. The illustrated embodiment has a measurement geometry, in which the three nominal observation directions 2, 3 and 4 extend at an angle of 15°, 45° and 110°, respectively, to the specular direction 1, wherein the second nominal illumination direction 3 coincides with the apparatus normal 0. The nominal observation direction 5 extends at an angle of 90° to the specular direction 1.

The lenses 21, 31, 41 and 51 can also be completely or partially omitted. Similarly, the illumination with parallel light is not mandatory.

In the shown embodiment, the illumination and pick-up beam paths are rectilinearly formed. However, it is also possible, e.g. for reasons of space, to fold one or more of the beam paths, thus to redirect them e.g. by means of mirror. It is only essential that the optical axes of the optical beam sections, which immediately lead to or from the measurement spot are in a common measurement plane.

Figure 7:
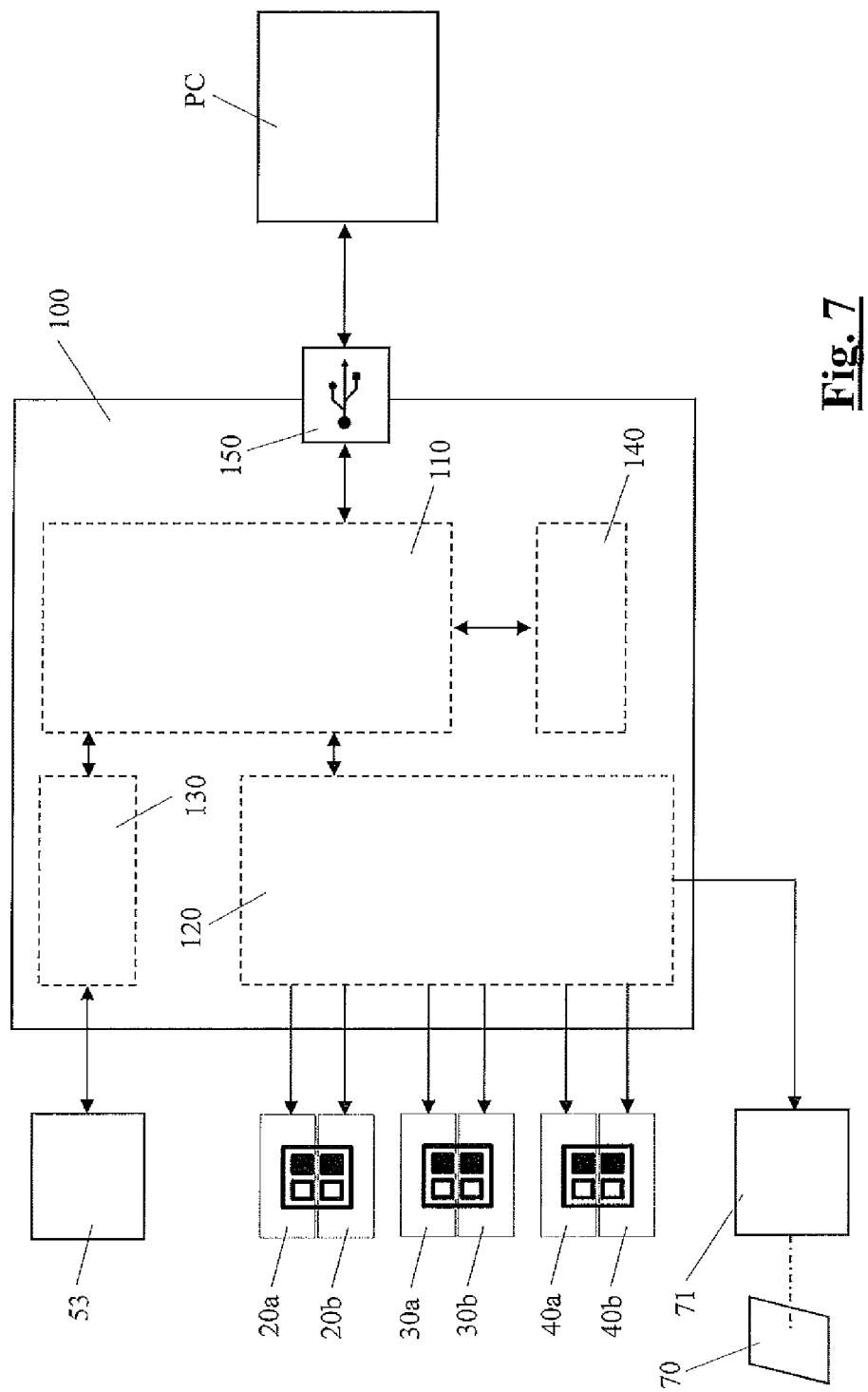
FIG. 7 shows a block diagram of the electronic control of the color measuring apparatus.

The illumination assemblies 20, 30 and 40 are controlled by the computer-based control 100 (FIG. 7). The latter also controls the pick-up assembly 50 or the spectrometer 53 thereof and processes the measurement signals thereof. The control 100 can display measurement results on the display assembly and receive control commands from the control organs. Further, it can communicate with an external computer via the mentioned interface, in particular transmit measurement data and receive commands and control data. More details are explained further below in association with FIG. 7.

So far, the described color measuring apparatus basically corresponds to the color measuring apparatus of this type disclosed in the documents EP 2 703 789 A1 and EP 2 728 342 A1 such that the expert does not need further explanation in respect thereto.

The present invention does not deal with the basic measurement technology as such and the evaluation of the measurement results, but with the problems of the corruption of the measurement results caused by orientation or angular errors in particular of the illumination assemblies. In the following, this and the elimination of or compensation for such measurement corruptions according to the invention, respectively, is elaborated in more detail based on FIGS. 2-5.

According to the most essential basic idea of the invention, at least one of the illumination assemblies 20, 30 and 40 is composed of two or more illumination subassemblies 20a, 20b, 30a, 30b and 40a, 40b, respectively, which illuminate the measurement field MF of the measurement object MO in various illumination sub-directions 2a, 2b, 3a, 3b and 4a, 4b, respectively, relatively slightly deviating from the respective nominal illumination direction 2, 3 and 4, respectively. In the embodiment of FIGS. 2-5, each illumination assembly 20, 30 and 40 each includes two illumination subassemblies 20a, 20b, 30a, 30b and 40a, 40b, which each cast a parallel radiation beam to the measurement spot MF of the measurement object MO via the respectively common lenses 21, 31 and 41. Therein, the illumination subassemblies are positioned such that the one illumination subassembly 20a, 30a and 40a respectively illuminates the measurement spot MF in an illumination sub-direction 2a, 3a and 4a, respectively, which deviates in the one direction from the respective nominal illumination direction 2, 3 and 4, respectively, by a small angle of $-\Delta\varepsilon/2$, and the other illumination subassembly 20b, 30b and 40b respectively illuminates the measurement spot MF in an illumination sub-direction 2b, 3b and 4b, respectively, which deviates in the other direction from the respective nominal illumination direction 2, 3 and 4, respectively by a small angle of $+\Delta\varepsilon/2$. Thus, within an illumination assembly 20, 30 and 40, respectively, the respective illumination sub-directions 2a, 2b, 3a, 3b and 4a, 4b, respectively, enclose the respective nominal illumination directions 2, 3, and 4, respectively, between them, wherein the nominal illumination directions do not necessarily have to be located centrally between the respective illumination sub-directions, but can also asymmetrically divide the angular interval $\Delta\varepsilon$ between the two illumination sub-directions. The angular interval or the differential angle $\Delta\varepsilon$ between the two illumination sub-directions 2a, 2b, 3a, 3b, 4a, 4b within an illumination assembly 20, 30 and 40, respectively, is comparatively small in proportion to the angles between the nominal illumination directions 2, 3 and 4 and preferably is not more than 4°-8°, thus $\pm 2°$ to $\pm 4°$ with symmetrical deviation from the respective nominal illumination direction 2, 3 and 4, respectively. For avoiding drawing overload, the angular interval or the differential angle $\Delta\varepsilon$ is only registered in the illumination assembly 20 in FIG. 2.

For the sake of simplicity, the following explanations are effected only in connection with the illumination assembly 20. However, they also apply in analogous manner to the two other illumination assemblies 30 and 40.

FIG. 3 shows the construction of the illumination assembly 20. It includes the two already mentioned illumination subassemblies 20a and 20b next to each other in low distance in the measurement plane denoted by MP. Each of the two illumination subassemblies 20a and 20b includes a light source, which is respectively composed of two light emitting diodes (LEDs) 22a, 23a and 22b, 23b, respectively, in the example here. The two light emitting diodes 22a, 23a and 22b, 23b, respectively, of the light sources are disposed next to each other in the direction perpendicular to the measurement plane MP, thus are angularly offset—measured in a projection to the measurement plane—by the same amount with respect to the nominal illumination direction 2.

The number of the light emitting diodes per light source depends on the spectral range to be measured and the spectral characteristics of the light emitting diodes. In the extreme case, a single (white) light emitting diode can be sufficient, in other cases of application, multiple light emitting diodes can also be required, in particular e.g. also UV light emitting diodes. However, one white light emitting diode 22a and 22b, respectively, and one blue light emitting diode 23a and 23b, respectively, are generally respectively sufficient.

FIGS. 4 and 5 illustrate the illumination conditions with the two illumination subassemblies 20a and 20b. The two illumination subassemblies 20a and 20b not illustrated in these figures generate (in combination with the lens 21 commonly associated with them) two parallel radiation beams 2as and 2bs in the direction of the respective illumination sub-direction 2a and 2b, respectively. The illumination pattern arising on the measurement object is apparent from FIG. 5. The two radiation beams 2as and 2bs overlap in the area of the measurement spot MF and illuminate the latter. From the measurement spot MF, one beam 5s of the measurement light radiated back enters the pick-up assembly 50 not illustrated in FIGS. 4 and 5 in observation direction 5.

From the above explanations, it is clear that the one illumination subassembly 20a illuminates the measurement spot MF at a too small angle with respect to the nominal illumination direction 2 and the other illumination subassembly 20b illuminates the measurement spot MF at a too large angle with respect to the nominal illumination direction 2. Therefore, the measurement results (spectral reflectivities) achieved in these two illumination sub-directions will usually deviate in both cases from those measurement results, which would be achieved with illumination exactly in the direction of the nominal illumination direction. Here, the main idea of the invention now applies: by a weighted mixture of the measurement results with illumination in the two illumination sub-directions 2a and 2b, measurement results can be achieved, which exactly coincide with those measurement results, which would be achieved with illumination exactly in the direction of the nominal illumination direction. Therein, it does not play any role how exactly the illumination assembly 20 or the remaining illumination assemblies 30 and 40 are oriented relative to their respective nominal illumination directions 2 and 3 and 4, respectively, if the latter are only respectively within the angular intervals $\Delta\varepsilon$ between the illumination sub-directions 2a, 2b, 3a, 3b and 4a, 4b, respectively.

If $r_a(i, \lambda)$ is the reflectivity measured with illumination in illumination sub-direction 2a, 3a and 4a, respectively, for the wavelength $\lambda$, wherein i stands for one of the three illumination assemblies 20, 30 and 40, and if $r_b(i, \lambda)$ is the reflectivity measured with illumination in illumination sub-direction 2a, 3a and 4a, respectively, for the wavelength $\lambda$, wherein i again stands for one of the three illumination assemblies 20, 30 and 40, then, the corrected reflectivity $r_k(i, \lambda)$ results computationally for the wavelength $\lambda$ according to the formula:

$$r_k(i,\lambda)=g_i*r_a(i,\lambda)+(1-g_i)*r_b(i,\lambda)$$

wherein $g_i$ is a weighting factor from 0 to 1 empirically determined separately for each illumination assembly. With a weighting factor approaching 0, the corrected reflectivity rk(i, $\lambda$) will approach the reflectivity $r_b(i, \lambda)$ measured in the illumination sub-direction 2b, 3b and 4b, respectively, and with a weighting factor approaching 1, the corrected reflectivity $r_k(i, \lambda)$ will approach the reflectivity $r_a(i, \lambda)$ measured in the illumination sub-direction 2a, 3a and 4a, respectively. The weighting factor $g_i$ thus effects an angular displacement of the metrologically effective illumination direction within the angular interval $\Delta\varepsilon$ between the respective two illumination sub-directions 2a, 2b, 3a, 3b and 4a, 4b, respectively.

In a particular implementation of the invention, the weighting factor $g_i$ can also be determined separately for each wavelength $\lambda$. In a further implementation, the weighting factor can also be outside of the range 0 to 1. Generally, the interpolation or extrapolation can also be performed for more than two sampling points as long as the sum of the weights for the individual spectra is normalized. The above explained calculation requires two separated measurement operations for each illumination assembly in each one of the two (or possibly even multiple) illumination sub-directions 2a, 2b, 3a, 3b and 4a, 4b. According to a further important aspect of the invention, this can be considerably simplified and correspondingly temporally shortened in that the weighting is performed in the measurement operation itself.

As in the known color measuring apparatus of this type, the measurement operation is principally effected such that—separately for each illumination channel (illumination assemblies 20, 30, 40)—by means of the pick-up assembly 50 a complete spectrum with a plurality of sampling points (wavelength ranges of e.g. each 10 . . . 20 nm width) is captured over the wavelength range of interest (mostly visible spectrum plus near UV). Thereto, the spectrometer 53 is activated by the control 100 for a certain time window $T_S$ (set in measurement readiness) and the light source of the respective illumination assembly is activated or turned on for a certain period of time within this time window. The time window $T_S$ corresponds to the integration time of the spectrometer. In variation of this general measurement scheme, according to the invention—again separately for each illumination channel—within the time window $T_S$, in which the spectrometer 53 is switched to the active state, both illumination subassemblies 20a, 20b and 30a, 30b and 40a, 40b, respectively are each activated for an individual activation period of time $t_a$ and $t_b$, respectively (i.e. their associated light emitting diode light source is turned on), wherein the activation does not necessarily have to be simultaneously effected, but the activation periods of time usually overlap each other. The activation periods of time are determined according to the formula:

$$t_a=G_i*T_0 \text{ and } t_b=(1-G_i)*T_0$$

wherein $G_i$ is a weighting factor from 0 to 1 and $T_0$ is a preset maximum activation period of time $<=T_S$. From the formula, it becomes immediately clear that with a weighting factor $G_i$ approaching 0, the measurement result is increasingly determined by the illumination by the illumination subassembly 20b and 30b and 40b, respectively, and conversely, with a weighting factor $G_i$ approaching 1, the measurement result is increasingly determined by the illumination by the illumination subassembly 20a and 30a and 40a, respectively. By selection of the weighting factor $G_i$ or of the ratio of the activation periods of time $t_a$ and $t_b$ of the two illumination subassemblies, thus, each arbitrary effective angular displacement can be adjusted within the limits given by the two illumination sub-directions. FIG. 6 illustrates these ratios. In a particular implementation of the invention, the weighting of the period of time can also be expanded to more than two illumination subassemblies as long as the sum of the weights is normalized.

Basically, it is also possible to orient the illumination subassemblies such that they do not enclose the respective nominal illumination direction between them, but are all on the same side next to the latter. In this case, the above outlined interpolation measures become extrapolation measures in analogous manner.

In FIG. 6, next to the main time window $T_S$, a second, narrower (shorter in time) time window $T_{S2}$ is also illustrated, within which a second measurement is respectively performed under otherwise identical conditions, wherein the activation periods of time of the two illumination subassemblies are denoted by $t_{a2}$ and $t_{b2}$ and their mutual ratio is the same as within the first time window $T_S$. The measurements performed within this shorter time window $T_{S2}$ are required for the optimum dynamic adaptation of the spectrometer 53. In particular in the measurement on samples with effect colors, with illumination directions near the specular direction (glancing angle), the reflectivities can become as high as the integration duration of the spectrometer must be shortened in order not to overload it. In a particular embodiment, more than two time windows can also be employed.

In FIG. 7, the cooperation of the individual components of the color measuring apparatus according to the invention is illustrated in a block diagram. The already mentioned computer-based control 100 includes a microcontroller 110, a hardware control stage 120, a spectrometer control stage 130, a data storage 140 and a USB interface 150 as the most important functional units, wherein the microcontroller 110 coordinates and controls the entirety and is also concerned with the communication with an external computer PC connected via the USB interface 150.

The hardware control stage 120 controls the illumination assemblies and the illumination subassemblies 20a, 20b, 30a, 30b, 40a, 40b thereof, respectively, i.e. turns on and off, respectively, the light sources contained therein. In addition, the hardware control stage 120 also controls a drive 71, by which a white tile 70 can be introduced into and again removed from the measurement beam path of the color measuring apparatus, respectively.

The spectrometer control stage 130 activates the spectrometer 53 and reads out the measurement data generated by it, conditions it and converts it into digital measurement signals (spectral reflectivities).

The (non-volatile) data storage 140 substantially contains adjustment parameters for the color measuring apparatus. In particular, the durations of the time windows for the spectrometer and the activation periods of time for the individual illumination subassemblies also belong thereto.

Before the color measuring apparatus is ready to use, it is first calibrated based on dark measurements and measurements on a white tile (white reference) in a manner known per se. Therein, the measurements on the white tile are separately performed for each illumination assembly and each illumination subassembly, respectively.

In a further step, the color measuring apparatus is profiled. Thereby, it is understood that its adjustment parameters are adjusted such that the color measuring apparatus provides measurement results, which match those of a reference color measuring apparatus as exactly as possible. The determination and adjustment of the adjustment parameters are effected under the control of the external computer PC based on comparison measurements. The adjustment parameters determined therein are then stored in the data storage 140. As already mentioned, in particular the activation periods of time of the individual illumination subassemblies also belong to the adjustment parameters.

The mentioned profiling can be absolute or relative. By absolute profiling, the adaptation to a highly precise reference color measuring apparatus (with the same measurement geometry) is to be understood. With a relative profiling, the adjustment of the parameters is effected with regard to the adaptation to any usually not so precise or error-prone target color measuring apparatus (with the same measurement geometry) as exact as possible. If the illumination assemblies of the target color measuring apparatus are (slightly) erroneously aligned, then, the color measuring apparatus according to the invention can emulate these misalignments by corresponding choice of its adjustment parameters such that the color measuring apparatus according to the invention and the target color measuring apparatus provide (nearly) exactly the same measurement results. This relative profiling is e.g. advantageous if existing color measuring apparatus are to be supplemented or replaced by new color measuring apparatus, but a considerable amount of measurement data has already been generated by means of the existing color measuring apparatus and this measurement data also is to be further usable. In these cases, the new color measuring apparatus must provide measurement results consistent with the existing color measuring apparatus.

As already mentioned above, the illumination assemblies 20, 30 and 40 also can each have more than two illumination subassemblies. In FIG. 8, an illumination assembly 20' with 5 illumination subassemblies 20a, 20b, 20c, 20d and 20e is for example illustrated, wherein each of these illumination subassemblies in turn includes two light emitting diodes as light source. The adjustment of the metrologically effective illumination direction is also effected in analogous manner by adequate choice of the weighting of the individual exposures via corresponding individual choice of the activation periods of time of the individual illumination subassemblies.

FIGS. 9 and 10 illustrate a further advantage allowed by the formation of the illumination assemblies with multiple, e.g. as shown in FIG. 8 transversely to the measurement plane, with each five illumination subassemblies.

If only the central illumination subassembly 20c is activated as in FIG. 9, all of the beams extend nearly parallel as shown to the right of the telecentric lens 21. The distribution of the luminance on the measurement field corresponds to the curve 25' shown rightmost in FIG. 9. If all of the illumination subassemblies are activated, the beam directions extend less collimated as shown to the right of the telecentric lens 21 in FIG. 10. The distribution of the luminance over the measurement spot rather corresponds to the curve 25" shown rightmost in FIG. 10. This corresponds to an aperture stop in effect.

With the aid of the inner illumination subassemblies 20b and 20d, with small field angle as described above, the effective illumination direction can be adjusted (FIG. 9). With activation also of the outer illumination subassemblies 20a and 20e and possibly also of the center illumination subassembly 20c, in contrast, a larger field angle is generated (FIG. 10). According to number of activated illumination subassemblies, thereby, the aperture can be optimally adjusted.

In the illustrated embodiment, all of the three illumination assemblies are each divided in two illumination subassemblies. However, it is also possible to form only one or a single one of the illumination assemblies with illumination subassemblies. This is particularly important in that illumination assembly, which is closest to the specular direction (glancing angle), since the influence of misalignments (angular errors) is most critical near the specular direction.

A further advantage of the invention is in that by individual activation of each illumination subassembly, not only the reflection factor of a sample in a certain arrangement, but also derivatives of the reflection factor of a sample in the direction of the illumination angle can be determined. This is a further criterion to differentiate material samples and can for example render the selection of varnish samples from a database more robust. The derivative can for example be determined by Lagrange interpolation with the aid of the sampling points given by the individual measurement values and derivative of the resulting polynomial at the desired point. The calculation of the derivative can be internally effected by the control 100 or externally by the connected computer. As a particularly advantageous characteristic of the invention, it is not required that the illumination subassemblies are mounted with high precision, it is sufficient to be able to precisely measure their position relative to the nominal illumination angle.

The measurement assembly MA can also be inversely formed with respect to illumination and observation assemblies. In the specific case, this means that the illumination of the measurement object would only be effected in a defined illumination direction and therefore the pick-up of the measurement light radiated back would be effected by means of three pick-up assemblies in three different observation directions, wherein at least one pick-up assembly would include at least two pick-up subassemblies in analogous manner. Of course, any combinations of one or more illumination assemblies and one or more pick-up assemblies are also possible. The weighting of the measurement results of the at least two pick-up subassemblies can then again be effected either computationally or by corresponding adjustment of the activation windows (integration periods of time) of the pick-up subassemblies. The weighting is of course separately effected for each pick-up assembly provided with pick-up subassemblies, and if two or more illumination assemblies are present, also individually for each of these illumination assemblies.

In FIG. 11, such an alternative embodiment of the color measuring apparatus according to the invention is schematically illustrated. Here, the color measuring apparatus includes a single illumination assembly 220 and a single pick-up assembly 250, which in turn includes two pick-up subassemblies 250a and 250b. Each pick-up subassembly includes a light guide 252a and 252b, respectively, and a spectrometer 253a and 253b, respectively.

The illumination assembly 220 illuminates the measurement object MO in an illumination direction 202. The two pick-up subassemblies 250a and 250b receive measurement light radiated from the measurement object MO from two observation directions 205a and 205b, respectively, which enclose a nominal observation direction 205 between them.

Although the present invention has been described with reference to exemplary embodiments thereof, the present invention is not limited by or to such exemplary embodiments. Rather, the present invention may be modified, refined and/or enhanced without departing from the spirit or scope of the present invention.

The invention claimed is:

1. A color measuring apparatus with illumination angle error compensation comprising:
    a measurement assembly, which includes at least one illumination assembly, the illumination assembly including at least two illumination subassemblies each including a light source generating substantially parallel illumination light, the illumination assembly being oriented to illuminate a measurement spot of a measurement object from a first preset nominal illumination direction, each illumination subassembly illuminating the measurement spot from illumination sub-directions that differ from the nominal illumination direction by angles of no more than 4°,
    a pick-up assembly for capturing the measurement light radiated back from the measurement spot and for converting the same into corresponding electrical signals; and
    a computer-based control with commands to:
        individually control the activation durations of the illumination subassemblies within each one illumination assembly; and
        form a sum of weighted illumination measurements from at least one pick-up assembly measurement from two or more illumination subdirections of an illumination assembly.

2. The color measuring apparatus according to claim 1, wherein the illumination sub-directions enclose the first nominal illumination direction between them.

3. The color measuring apparatus according to claim 1, wherein the illumination sub-directions are angularly offset to each other by an angle ($\Delta\varepsilon$) of 4°-8°.

4. The color measuring apparatus according to claim 1, wherein the illumination assembly includes maximally five illumination subassemblies, which illuminate the measurement spot from different illumination sub-directions near each other and therein enclose a nominal illumination direction between them.

5. The color measuring apparatus according to claim 1, further comprising at least one further illumination assembly, which illuminates the measurement spot substantially from a further preset nominal illumination direction different from the first preset nominal illumination direction.

6. The color measuring apparatus according to claim 5, wherein the at least one further illumination assembly includes at least two illumination subassemblies, which illuminate the measurement spot from different illumination sub-directions near the further preset nominal illumination direction.

7. The color measuring apparatus according to claim 1, wherein the light source of the illumination subassemblies is composed of at least one light emitting diode.

8. The color measuring apparatus according to claim 1, wherein the light source of the illumination subassemblies is composed of two or more light emitting diodes with different emission spectra.

9. The color measuring apparatus according to claim 1, wherein the control is further configured to operate the pick-up assembly.

10. The color measuring apparatus according to claim 1, wherein the control is formed to individually control the activation durations of the illumination subassemblies within each one illumination assembly.

11. The color measuring apparatus according to claim 1, wherein the control is further formed to activate the illumination subassemblies thereof, respectively, and the pick-up assembly for at least two differently long measurement durations.

12. The color measuring apparatus according to claim 1, further comprising means for calculating derivatives of the reflection measurement signals for a sample generated from individual activation of illumination subassemblies at positions relative to the angle of a nominal illumination direction.

13. The color measuring apparatus according to claim 1, wherein the at least two illumination subassemblies illuminate the measure spot with parallel illumination light.

14. The color measuring apparatus according to claim 1, wherein the control communicates with an external computer.

15. The color measuring apparatus according to claim 1, wherein the control computes derivatives of the reflection measurement signals for a sample generated from individual activation of illumination subassemblies at positions relative to a nominal illumination angle.

16. The color measuring apparatus of claim 1, wherein the illumination subdirections for an illumination subassembly are in a common measurement plane with an observation direction of the pickup assembly.

17. A color measuring apparatus with illumination angle error compensation comprising:
 a measurement assembly, including:
  a first illumination assembly, the first illumination assembly including at first and second illumination subassemblies each including a light source generating substantially parallel illumination light, the first illumination assembly being oriented to illuminate a measurement spot of a measurement object from a first preset nominal illumination direction, the first and second illumination subassemblies illuminating the measurement spot with illumination sub-directions that are angularly offset from each other by no more than 8°;
  a second illumination assembly, the second illumination assembly including at third and fourth illumination subassemblies each including a light source generating substantially parallel illumination light, the second illumination assembly being oriented to illuminate the measurement spot of the measurement object from a second preset nominal illumination direction, the third and fourth illumination subassemblies illuminating the measurement spot with illumination sub-directions that are angularly offset from each other by no more than 8°;
 a pick-up assembly for capturing the measurement light radiated back from the measurement spot and for converting the same into corresponding electrical signals, wherein the optical axes of the first, second, third, and fourth illumination subassemblies and the pick-up assembly which immediately lead to or from the measurement spot are in a common measurement plane; and
 a computer-based control with commands to:
  individually control the activation durations of the illumination subassemblies within each one illumination assembly; and
  form a sum of weighted illumination measurements from at least one pick-up assembly measurement from two or more illumination subdirections of an illumination assembly.

18. The color measuring apparatus of claim 17 wherein the first nominal illumination direction and second nominal illumination direction are angularly offset from each other by at least 30°.

\* \* \* \* \*